United States Patent
Horiuchi et al.

(10) Patent No.: US 12,336,862 B2
(45) Date of Patent: Jun. 24, 2025

(54) ULTRASONOGRAPHY APPARATUS, MAMMOGRAPHY APPARATUS, AND CONTROL PROGRAM

(71) Applicant: FUJIFILM Corporation, Tokyo (JP)

(72) Inventors: Hisatsugu Horiuchi, Kanagawa (JP); Lisako Nobuyama, Kanagawa (JP); Masataka Sugahara, Kanagawa (JP); Koji Taninai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/440,923

(22) Filed: Feb. 13, 2024

(65) Prior Publication Data

US 2024/0285262 A1 Aug. 29, 2024

(30) Foreign Application Priority Data

Feb. 27, 2023 (JP) ................. 2023-028962

(51) Int. Cl.
| | | |
|---|---|---|
| *A61B 8/08* | (2006.01) | |
| *A61B 6/00* | (2024.01) | |
| *A61B 6/04* | (2006.01) | |
| *A61B 6/50* | (2024.01) | |
| *A61B 8/00* | (2006.01) | |

(52) U.S. Cl.
CPC ............. *A61B 8/54* (2013.01); *A61B 6/0414* (2013.01); *A61B 6/4417* (2013.01); *A61B 6/502* (2013.01); *A61B 8/0825* (2013.01); *A61B 8/403* (2013.01); *A61B 8/4272* (2013.01); *A61B 8/4281* (2013.01); *A61B 8/429* (2013.01); *A61B 8/483* (2013.01); *A61B 8/5261* (2013.01)

(58) Field of Classification Search
CPC ........ A61B 8/4281; A61B 8/429; A61B 8/403
See application file for complete search history.

(56) References Cited

U.S. PATENT DOCUMENTS

| | | | |
|---|---|---|---|
| 2010/0217161 A1* | 8/2010 | Shalgi | A61B 5/6843 601/2 |
| 2017/0035361 A1 | 2/2017 | Yamamoto | |
| 2017/0245823 A1* | 8/2017 | Arai | A61B 6/4417 |
| 2019/0090836 A1 | 3/2019 | Arai et al. | |
| 2019/0175144 A1* | 6/2019 | O'Brien | A61B 8/0816 |
| 2020/0305836 A1 | 10/2020 | Arai et al. | |
| 2023/0099356 A1 | 3/2023 | Arai et al. | |

FOREIGN PATENT DOCUMENTS

| | | |
|---|---|---|
| JP | 2015-205041 A | 11/2015 |
| JP | 2017-153571 A | 9/2017 |
| JP | 2020-162931 A | 10/2020 |

* cited by examiner

*Primary Examiner* — Colin T. Sakamoto
(74) *Attorney, Agent, or Firm* — Studebaker Brackett PLLC

(57) ABSTRACT

An ultrasonography apparatus includes: a processor configured to detect, from an image obtained by capturing a breast, a region of breast to which an acoustic matching member is not applied, the acoustic matching member being a member for reducing a difference in acoustic impedance between an ultrasound probe which outputs an ultrasonic wave to the breast and the breast; and an output unit that outputs a warning in a case where the region is detected by the processor.

12 Claims, 8 Drawing Sheets

ULTRASONOGRAPHY APPARATUS, MAMMOGRAPHY APPARATUS, AND CONTROL PROGRAM

CROSS-REFERENCE TO RELATED APPLICATION

This application claims priority from Japanese Patent Application No. 2023-028962, filed Feb. 27, 2023, the disclosure of which is incorporated herein by reference in its entirety.

BACKGROUND

Technical Field

The present disclosure relates to an ultrasonography apparatus, a mammography apparatus, a control method and a non-transitory storage medium storing a program.

Related Art

An ultrasonography apparatus that captures an ultrasound image of a breast by scanning a breast of an examinee with an ultrasound probe.

JP2020-162931A discloses an imaging member including a compression member that compresses a breast of an examinee and an ultrasound imaging member, which has a first surface on which an acoustic matching member having fluidity is provided and in which a second surface opposite to the first surface is provided on a surface of the compression member opposite to the surface in contact with the breast via a coupling material having fluidity lower than the fluidity of the acoustic matching member.

JP2017-153571A discloses a medical imaging apparatus that acquires a type of an acoustic matching member that is inserted between a compression plate and a breast in a case where an ultrasound image of the breast is captured.

JP2015-205041A discloses a test subject information acquisition apparatus including a level adjustment mechanism configured such that a level of a surface of an acoustic matching material can be set to a position higher than a boundary between a test subject holding member and a base.

In a case where a tumor is found using a high-density mammary gland, the tumor may be more easily found in an ultrasonography examination than in a mammography apparatus. In a case of examining the presence or absence of a tumor in a breast using an ultrasonic wave, in order to reduce a difference in acoustic impedance between an ultrasound probe and the breast, an acoustic impedance member is applied to the breast in advance.

In a case where there is an application omission portion of the acoustic impedance member within an examination range, an ultrasound image at a position corresponding to the application omission portion becomes unclear.

Therefore, in a case where an examiner is manually capturing an ultrasound image while holding an ultrasound probe in the hand, the examiner confirms an application state of the acoustic impedance member and, in a case where there is an application omission portion, applies the acoustic impedance member to the application omission portion.

However, in the ultrasonography apparatus in the related art in which the examination process is automated, the examiner cannot confirm the application state of the acoustic impedance member. As a result, an ultrasound image at a position corresponding to the application omission portion may become unclear.

SUMMARY

The present disclosure has been made in view of the above circumstances, and an object of the present disclosure is to provide an ultrasonography apparatus, a mammography apparatus, a control method and a non-transitory storage medium storing a program capable of confirming an application state of an acoustic impedance member on a breast before an ultrasound image is captured.

According to a first aspect, there is provided an ultrasonography apparatus including: a processor configured to detect, from an image obtained by capturing a breast, a region of breast to which an acoustic matching member is not applied, the acoustic matching member being a member for reducing a difference in acoustic impedance between an ultrasound probe which outputs an ultrasonic wave to the breast and the breast; and an output unit that outputs a warning in a case where the region is detected by the processor.

According to a second aspect, in the ultrasonography apparatus according to the first aspect, the ultrasonography apparatus further includes: a compression plate that compresses the breast on an imaging table in a case where an ultrasound image is captured using the ultrasound probe. In a case where the warning is output by the output unit, the processor is configured to release a compression force of the compression plate that compresses the breast.

According to a third aspect, in the ultrasonography apparatus according to the second aspect, the processor is configured to detect the region from a predetermined range in the image, which is predetermined as a breast diagnosis location by using an ultrasonic wave.

According to a fourth aspect, in the ultrasonography apparatus according to the third aspect, the ultrasonography apparatus further includes: an imaging table on which the breast is placed for imaging, wherein the processor is configured to set the predetermined range to be a range of the breast pressed against the imaging table by the compression plate, and to detect the region.

According to a fifth aspect, in the ultrasonography apparatus according to the fourth aspect, a loading surface of the imaging table on which the breast is placed is painted in a color different from a color of the breast.

According to a sixth aspect, in the ultrasonography apparatus according to the third aspect, the processor is configured to set, each time a type of the compression plate is changed, the predetermined range to be a breast compression range that is associated in advance with each type of the compression plate, and to detect the region.

According to a seventh aspect, in the ultrasonography apparatus according to the third aspect, the processor is configured to set the predetermined range to be a designated location in the image, and to detect the region.

According to an eighth aspect, in the ultrasonography apparatus according to the third aspect, the processor is configured to set the predetermined range to be a maximum movement range of the ultrasound probe in the image, and to detect the region.

According to a ninth aspect, in the ultrasonography apparatus according to any one aspect of the second aspect to the eighth aspect, the processor is configured to: detect a caution portion at which a degree of close contact between the acoustic matching member and at least one of the breast or the compression plate in a state where the breast is compressed by the compression plate is different from other portions, and in a case where the caution portion is detected, release a compression force of the compression plate that compresses the breast and then recompress the breast by the compression plate.

According to a tenth aspect, there is provided a mammography apparatus including: a radiation source that irradiates a breast with radiation; and the ultrasonography apparatus according to any one aspect of the first aspect to the third aspect.

According to an eleventh aspect, in the mammography apparatus according to the tenth aspect, the processor is configured to identify a breast diagnosis location by using an ultrasonic wave from a radiation image of the breast that is captured by the radiation emitted from the radiation source, and to detect the region from a range of the identified breast diagnosis location.

According to a twelfth aspect, there is provided a control method including: detecting, from an image obtained by capturing a breast, a region of breast to which an acoustic matching member is not applied, the acoustic matching member being a member for reducing a difference in acoustic impedance between an ultrasound probe which outputs an ultrasonic wave to the breast and the breast; and outputting a warning in a case where the region is detected.

According to a thirteenth aspect, there is provided a non-transitory storage medium storing a program that causes a computer to execute a control process, the control process including: detecting, from an image obtained by capturing a breast, a region of breast to which an acoustic matching member is not applied, the acoustic matching member being a member for reducing a difference in acoustic impedance between an ultrasound probe which outputs an ultrasonic wave to the breast and the breast; and outputting a warning in a case where the region is detected.

According to the present disclosure, it is possible to confirm an application state of an acoustic impedance member on a breast before an ultrasound image is captured.

DESCRIPTION OF THE EMBODIMENTS

Figure 1:
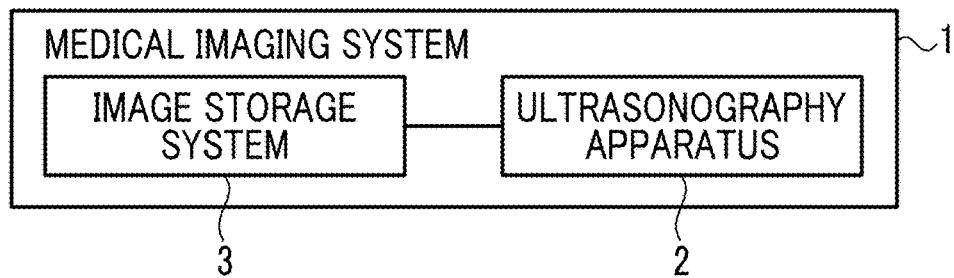
FIG. 1 is a diagram illustrating a configuration example of a medical imaging system according to a first embodiment.

Hereinafter, embodiments of the present disclosure will be described with reference to the drawings. The identical components and the identical processes are denoted by the identical reference numerals throughout the drawings, and redundant description will be omitted.

First Embodiment

FIG. 1 is a diagram illustrating a configuration example of a medical imaging system 1 according to a first embodiment. The medical imaging system 1 includes an ultrasonography apparatus 2 and an image storage system 3.

The ultrasonography apparatus 2 is an apparatus that captures an ultrasound image of a breast of an examinee as a subject by, for example, a medical worker such as an examination technician or a doctor.

The image storage system 3 is a system that stores the ultrasound images captured by the ultrasonography apparatus 2. The image storage system 3 extracts an ultrasound image corresponding to a request from the ultrasonography apparatus 2 or a console 6 (refer to FIG. 10) to be described later, from the stored ultrasound images, and transmits the extracted ultrasound image to a request source apparatus. A specific example of the image storage system 3 is a picture archiving and communication system (PACS).

Figure 2:
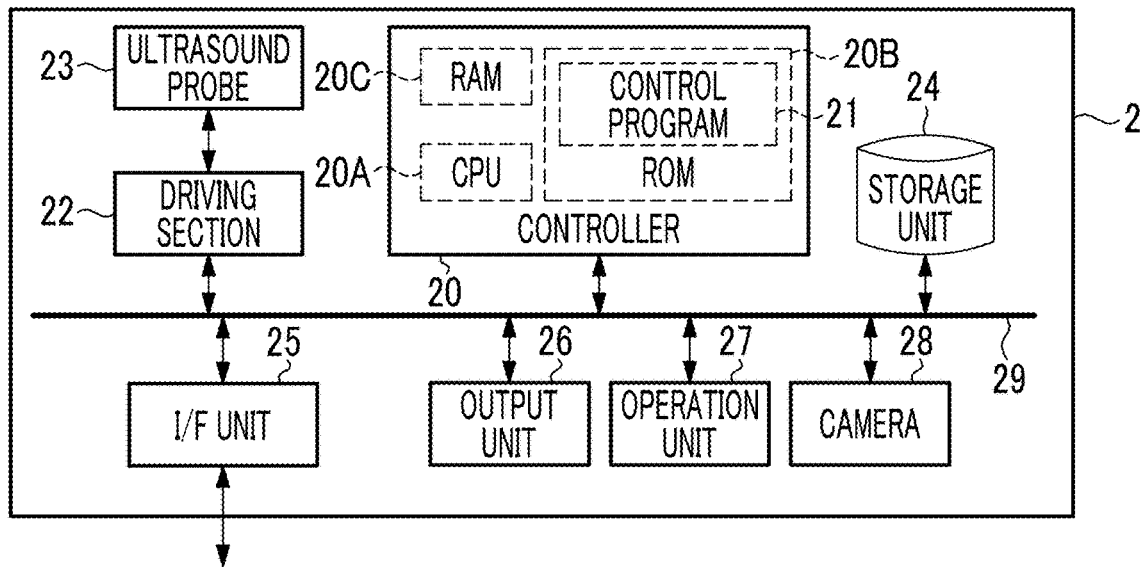
FIG. 2 is a diagram illustrating a configuration example of an ultrasonography apparatus.

First, a configuration example of the ultrasonography apparatus 2 will be described. FIG. 2 is a diagram illustrating a configuration example of the ultrasonography apparatus 2.

As illustrated in FIG. 2, the ultrasonography apparatus 2 includes a controller 20, a driving section 22, an ultrasound probe 23, a storage unit 24, an interface (I/F) unit 25, an output unit 26, an operation unit 27, and a camera 28. The controller 20, the driving section 22, the ultrasound probe 23, the storage unit 24, the I/F unit 25, the output unit 26, the operation unit 27, and the camera 28 are connected to each other via a bus 29 to exchange various types of information.

The controller 20 controls an operation of the ultrasonography apparatus 2 based on an instruction from the medical worker. The controller 20 includes a central processing unit (CPU) 20A which is an example of a processor, a read only memory (ROM) 20B, and a random access memory (RAM) 20C. The ROM 20B stores in advance various programs including a control program 21 that is read by the CPU 20A to perform control for capturing an ultrasound image, and various parameters to be referred to in a case where the CPU 20A controls an operation of the ultrasonography apparatus 2. The RAM 20C is used as a temporary work area of the CPU 20A.

The ultrasound probe 23 outputs an ultrasonic wave to the subject, that is, the breast, acquires a reflected wave of the ultrasonic wave that is reflected by the breast, converts the acquired reflected wave into reflected wave data, and outputs the reflected wave data to the controller 20. The controller 20 that receives the reflected wave data generates an ultrasound image of the breast by using the reflected wave data which is received. In a case where an ultrasound image is captured, an acoustic matching member is applied on the breast.

The acoustic matching member is a member that is applied between a living body and an object other than the living body, for example, such as the ultrasound probe 23 and a breast, and has acoustic impedance close to the acoustic impedance of the living body. In a case where a space between the ultrasound probe 23 and the breast is filled with an acoustic impedance member having acoustic impedance close to the acoustic impedance of the living body, air is prevented from being flowed to the space between the ultrasound probe 23 and the breast, and the ultrasonic wave is more easily transmitted between the ultrasound probe 23 and the breast than in a case where the acoustic matching member is not used. Thus, a clearer ultrasound image can be obtained. The type of the acoustic matching member is not limited, and for example, a gel-type acoustic matching member or a jelly-type acoustic matching member is used. Alternatively, the acoustic matching member may be a liquid confined in a sealed bag.

The driving section 22 causes the ultrasound probe 23 to move in a direction along a chest wall of the examinee in a case where the breast is viewed from above, that is, in a lateral direction, and in a direction intersecting the chest wall of the examinee, that is, in a vertical direction under a control of the controller 20. That is, in the ultrasonography apparatus 2, even in a case where a medical worker does not move the ultrasound probe 23 to a diagnosis location while holding the ultrasound probe 23 in a hand, the controller 20 controls the driving section 22 to move the ultrasound probe 23. As will be described later, the driving section 22 also drives movable parts of a housing of the ultrasonography apparatus 2 configured to be movable so as to facilitate capturing of the ultrasound image of the breast, under a control of the controller 20.

The storage unit 24 stores the captured ultrasound images, various information, and the like. The storage unit 24 is an example of a storage device that maintains stored information even in a case where power supplied to the storage unit 24 is cut off. For example, a semiconductor memory such as a solid state drive (SSD) is used, or a hard disk may be used.

The I/F unit 25 transmits and receives various kinds of information to and from an external apparatus connected to a communication line (not illustrated) such as a local area network (LAN), by using wireless communication or wired communication. For example, the controller 20 transmits the captured ultrasound image to the image storage system 3 via the I/F unit 25.

The output unit 26 outputs, to the medical worker, information processed by the controller 20, such as a capturing status of the ultrasound image and a warning. Outputting the information means presenting the information in a state where the user can confirm the information. Therefore, for example, all of a form in which information is displayed on a display, a form in which information is printed on a recording medium such as paper by an image forming apparatus (not illustrated), and a form in which information is notified by voice via a speaker are examples of outputting information by the output unit 26.

The operation unit 27 is used by the medical worker to input, for example, instructions and various kinds of information related to capturing of an ultrasound image. An operation form of the operation unit 27 is not limited, and, for example, an operation by a switch, a touch panel, a touch pen, a mouse, or the like can be received.

The camera 28 is attached to a position where the entire breast diagnosis location is included in an angle of view, and captures an image of the breast including a position with which the ultrasound probe 23 comes into contact. An image of the breast captured by the camera 28 may be a visible image or an infrared image, and may be a still image or a motion picture. Hereinafter, an image of the breast captured by the camera 28 will be referred to as a "breast image", and will be distinguished from an ultrasound image obtained by the ultrasound probe 23. The breast image is an example of an image obtained by capturing the breast of the examinee with the camera 28.

Figure 3:
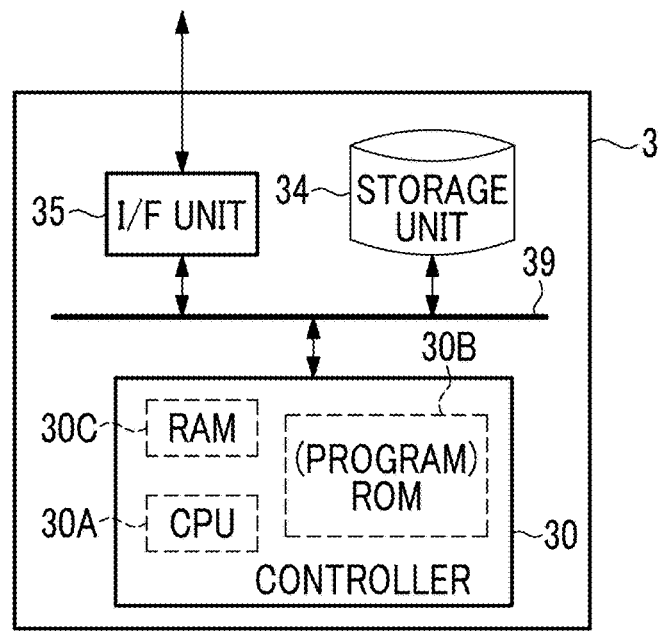
FIG. 3 is a diagram illustrating a configuration example of an image storage system.

On the other hand, FIG. 3 is a diagram illustrating a configuration example of the image storage system 3. As illustrated in FIG. 3, the image storage system 3 includes a controller 30, a storage unit 34, and an I/F unit 35. The controller 30, the storage unit 34, and the I/F unit 35 are connected to each other via a bus 39 such that various kinds of information can be exchanged.

The controller 30 controls an operation of the image storage system 3. The controller 30 includes a CPU 30A, a ROM 30B, and a RAM 30C. Various programs that are read by the CPU 30A to perform control related to storing of the ultrasound images and various parameters that are referred to by the CPU 30A to control an operation of the image storage system 3 are stored in the ROM 30B in advance. The RAM 30C is used as a temporary work area of the CPU 30A.

The storage unit 34 stores the ultrasound image in association with, for example, a capturing order or information related to the examinee. That is, the storage unit 34 functions as a database for the ultrasound images.

The I/F unit 35 transmits and receives various kinds of information to and from an external apparatus connected to a communication line such as a LAN, by using wireless communication or wired communication. For example, the controller 30 transmits a requested ultrasound image to the ultrasonography apparatus 2 via the I/F unit 35.

Figure 4:
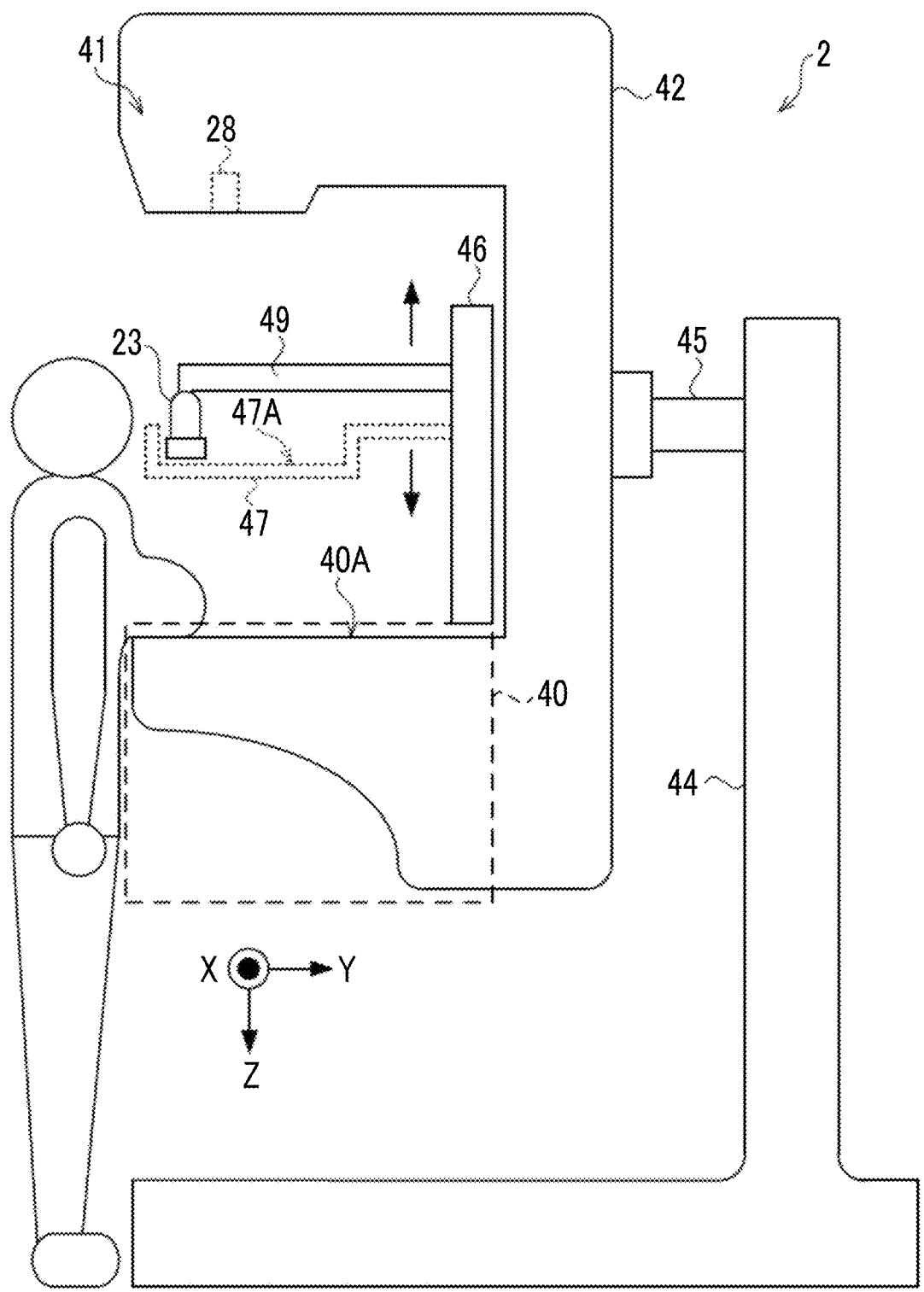
FIG. 4 is a diagram illustrating an example of an external appearance of the ultrasonography apparatus.

Next, an example of capturing of an ultrasound image of a breast by the ultrasonography apparatus 2 will be described. FIG. 4 is a diagram illustrating an example of an external appearance of the ultrasonography apparatus 2 in a case where the ultrasonography apparatus is viewed from a side.

The ultrasonography apparatus 2 includes an arm portion 42, a base 44, and a shaft portion 45. The arm portion 42 is held by the base 44 so as to be movable in an upward-downward direction (Z-axis direction). The shaft portion 45 connects the arm portion 42 to the base 44. The arm portion 42 can be relatively rotated with respect to the base 44, using the shaft portion 45 as a rotation axis.

The arm portion 42 is provided with an imaging table 40 on which the examinee places a breast for capturing of an ultrasound image of the breast and a driving unit 46. A surface of the imaging table 40 on which the examinee places a breast is referred to as a loading surface 40A.

The driving unit 46 moves the ultrasound probe 23 in a linear direction passing through both shoulders of the examinee, that is, a direction intersecting with an X-axis direction and a chest wall surface of the examinee, that is, a Y-axis direction orthogonal to an X-axis and a Z-axis, by using, for example, a movement rails 49.

Figure 5:
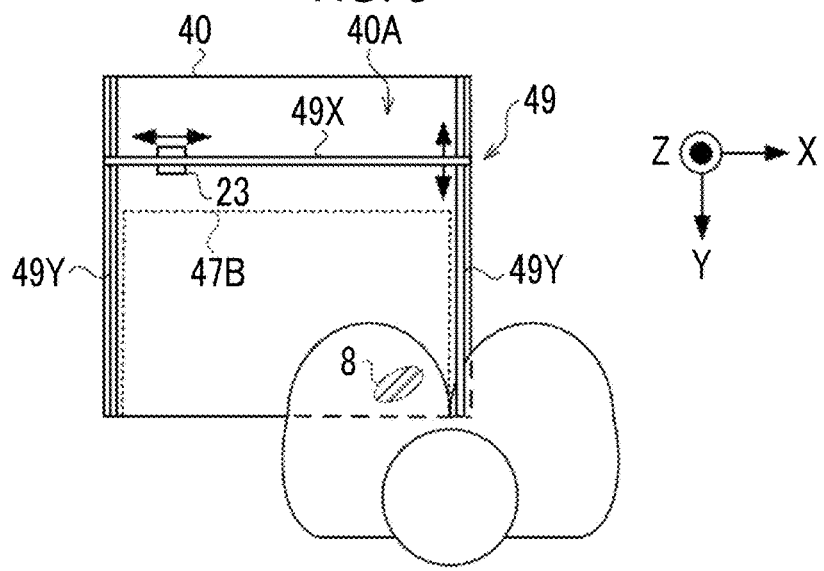
FIG. 5 is a diagram illustrating a state of an examinee placing a breast on a loading surface of an imaging table.

FIG. 5 is a diagram illustrating an example in which an examinee whose a breast is placed on the loading surface 40A is viewed from a position facing the loading surface 40A of the imaging table 40 in the Z-axis direction.

As illustrated in FIG. 5, the movement rail 49 is configured with one movement rail 49X extending along the X-axis direction and two movement rails 49Y extending along the Y-axis direction. The movement rails 49Y are provided along both ends of the loading surface 40A, and the driving unit 46 changes a position of the ultrasound probe 23 along the Y-axis direction by moving the movement rail 49X to which the ultrasound probe 23 is attached along the Y-axis direction. In addition, the driving unit 46 changes a position of the ultrasound probe 23 along the X-axis direction by moving the ultrasound probe 23 along the movement rail 49X. Hereinafter, a direction along the X-axis direction may be referred to as a "rightward-leftward direction", and a direction along the Y-axis direction may be referred to as a "forward-backward direction".

The method of driving the ultrasound probe 23 by using the driving unit 46 according to the present disclosure is an example, and the method of driving the ultrasound probe 23 is not limited as long as the position of the ultrasound probe 23 can be changed.

For example, the ultrasound probe 23 is attached to a support column (not illustrated) extending from the driving unit 46 toward a chest wall of the examinee, and the driving unit 46 may change the position of the ultrasound probe 23 by expanding and contracting the support column in the Y-axis direction and moving the support column in the X-axis direction.

In addition, as illustrated in FIG. 4, the driving unit 46 can also change a height of the ultrasound probe 23 by moving the movement rail 49 in the Z-axis direction. That is, the driving unit 46 drives the movement rail 49 according to an instruction of the driving section 22, and thus a position of the ultrasound probe 23 attached to the movement rail 49 is moved in each of the forward-backward direction, the rightward-leftward direction, and the upward-downward direction.

A compression plate 47 is attached to the driving unit 46. The compression plate 47 is a member that is moved in the upward-downward direction by the driving unit 46 and compresses the breast such that the ultrasonic wave can easily reach the diagnosis location. A region 47B illustrated by a dotted line of FIG. 5 indicates a breast compression range by the compression plate 47.

In this case, the ultrasound probe 23 comes into contact with an upper surface 47A of the compression plate 47, that is, a surface opposite to the surface of the compression plate 47 which comes into contact with the breast of the examinee, outputs an ultrasonic wave from the surface opposite to the surface of the compression plate 47, and acquires a reflected wave from the breast. Here, as an example, an example in which the compression plate 47 is not attached to the driving unit 46 is described.

For the movement direction of the compression plate 47, a direction in which the breast is compressed, that is, a direction in which the compression plate 47 approaches the loading surface 40A may be referred to as a "compression direction", and a direction in which compression of the breast is released, that is, a direction in which the compression plate 47 approaches the camera 28 may be referred to as a "compression release direction".

The movement of the ultrasound probe 23, the movement of the compression plate 47, and the movement and rotation of the arm portion 42 in the upward-downward direction are performed by a control of the controller 20 via the driving section 22.

The camera 28 is attached to, for example, an upper portion of the arm portion 42 facing the loading surface 40A as illustrated in FIG. 4 such that the entire breast diagnosis location is included in the angle of view. Therefore, in the arm portion 42, a portion located at an upper portion of the arm portion 42 in which the camera 28 is installed is also referred to as an "imaging unit 41".

In a case where an ultrasound image of the breast is captured by the ultrasound probe 23, an acoustic matching member is applied to the breast as described above. However, as illustrated in FIG. 5, in some cases, a portion in which the acoustic matching member is not applied, that is, an application omission portion 8 may occur.

Hereinafter, an operation of the ultrasonography apparatus 2 that captures an ultrasound image while confirming an application state of the acoustic matching member will be described in detail.

Figure 6:
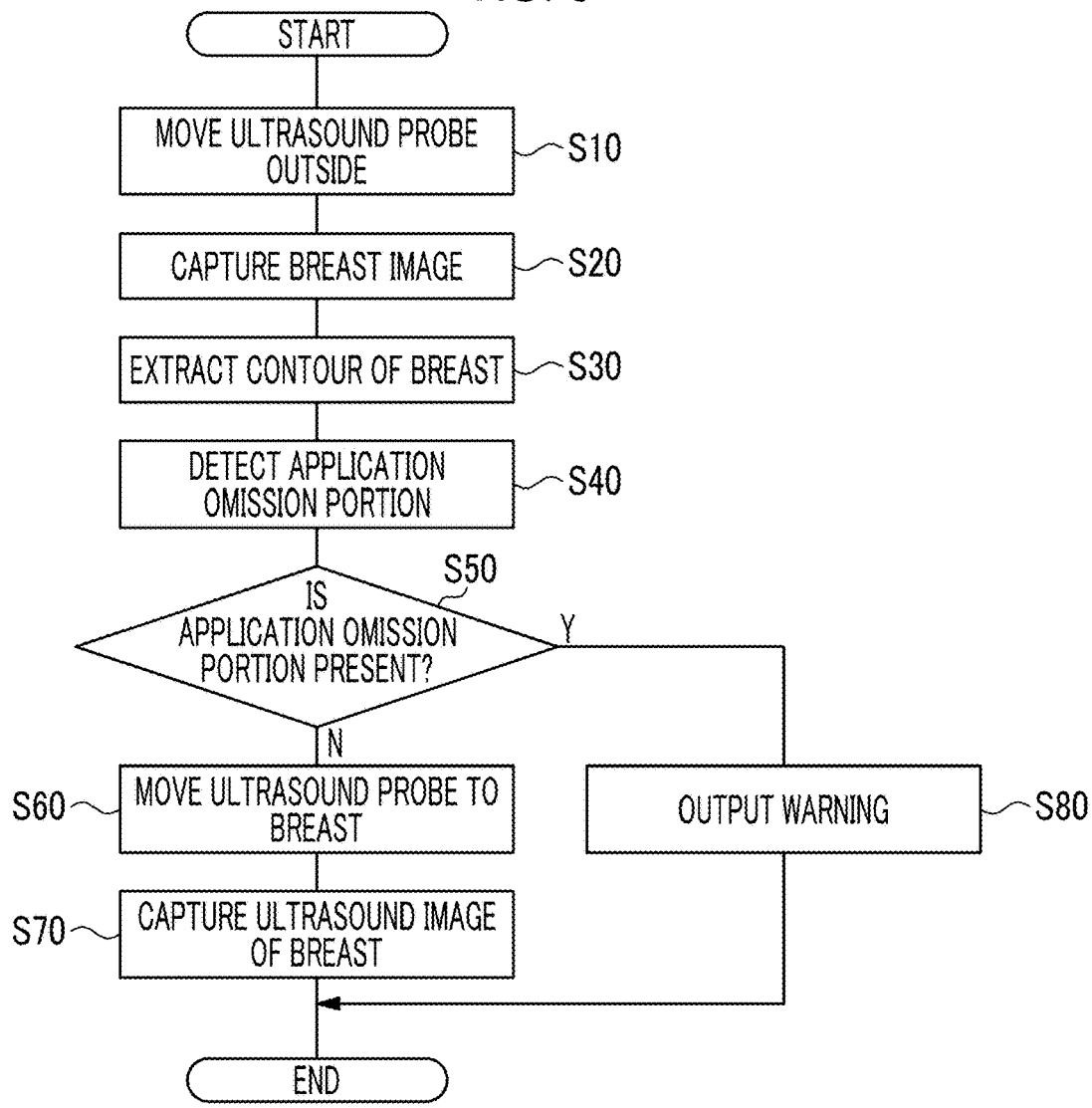
FIG. 6 is a flowchart illustrating an example of a flow of imaging processing executed by the ultrasonography apparatus.

FIG. 6 is a flowchart illustrating an example of a flow of imaging processing executed by the ultrasonography apparatus 2 in a case where an instruction to start capturing of an ultrasound image of the breast is received according to an operation of a medical worker via the operation unit 27. The CPU 20A of the ultrasonography apparatus 2 reads the control program 21 from the ROM 20B and executes imaging processing.

It is assumed that an acoustic matching member is applied to the breast of the examinee prior to capturing of an ultrasound image. The application of the acoustic matching member to the breast may be performed by a medical worker by hand, or may be performed by using an application unit (not illustrated) that automatically applies the acoustic matching member to the breast by the ultrasonography apparatus 2. In addition, as illustrated in FIG. 4, a state is assumed in which the examinee places the breast which is the subject on the loading surface 40A of the imaging table 40.

First, in step S10, the controller 20 moves the ultrasound probe 23 outside an imaging range of the camera 28 such that the ultrasound probe 23 is not included in the imaging range of the camera 28, by controlling the driving unit 46 via the driving section 22. For example, position information indicating a position outside the imaging range of the camera 28 is stored in advance in the ROM 20B.

In step S20, the controller 20 captures a breast image by controlling the camera 28.

In step S30, the controller 20 extracts a contour of the breast from the breast image captured by processing of step S20. For example, a known image processing method such as edge filter processing is used to extract the contour of the breast.

It is preferable to apply a color of the loading surface 40A to a color different from the skin color such that the contour of the breast can be easily extracted from the breast image. Before capturing of the breast image, a mat having a color different from the skin color may be laid on the loading surface 40A. The color different from the skin color is, for example, a color having a hue that is separated from the skin color by a predetermined angle or more in a color model such as an HSB color ring. As an example, it is preferable that the color of the loading surface 40A is separated from the skin color by, for example, 90 degrees or more. Therefore, a complementary color to the skin color is an example of a color different from the skin color.

In step S40, the controller 20 detects an application omission portion 8 of the acoustic matching member from a range within the contour of the breast extracted by processing of step S30. The range within the contour of the breast is an example of a predetermined range that is set as a diagnosis location.

For example, a known image processing method such as image recognition is used to detect the application omission portion 8. In image recognition, a difference in color is often used to detect a specific location. Thus, it is preferable to use an acoustic matching member colored in a color different from the skin color such that it is easy to distinguish the application omission portion 8 and a portion in which there is no application omission. In addition, in order to make it easier to understand the color of the acoustic matching member in the breast image, it is preferable to use an acoustic matching member having as low transparency as possible.

In step S50, the controller 20 determines whether or not there is an application omission portion 8 of the acoustic matching member in the breast. In a case where there is no application omission portion 8, the processing proceeds to step S60.

In step S60, the controller 20 moves the ultrasound probe 23 to a position where the ultrasound probe 23 comes into contact with the breast by controlling the driving unit 46 via the driving section 22.

In step S70, the controller 20 causes the ultrasound probe 23 to output an ultrasonic wave by controlling the ultrasound probe 23 via the driving section 22. Thereafter, the controller 20 causes the ultrasound probe 23 to scan the entire breast along the shape of the breast in a state where the ultrasound probe 23 is in contact with the breast and to capture an ultrasound image of the entire breast, by controlling the driving unit 46 via the driving section 22.

The controller 20 captures a plurality of ultrasound images in the process in which the ultrasound probe 23 performs scanning. Then, the controller 20 combines the ultrasound images into one ultrasound image, and generates an ultrasound image covering a range wider than a range of each of the ultrasound images, by using scanning position information of the ultrasound probe 23 associated with each of the ultrasound images.

Figure 7:
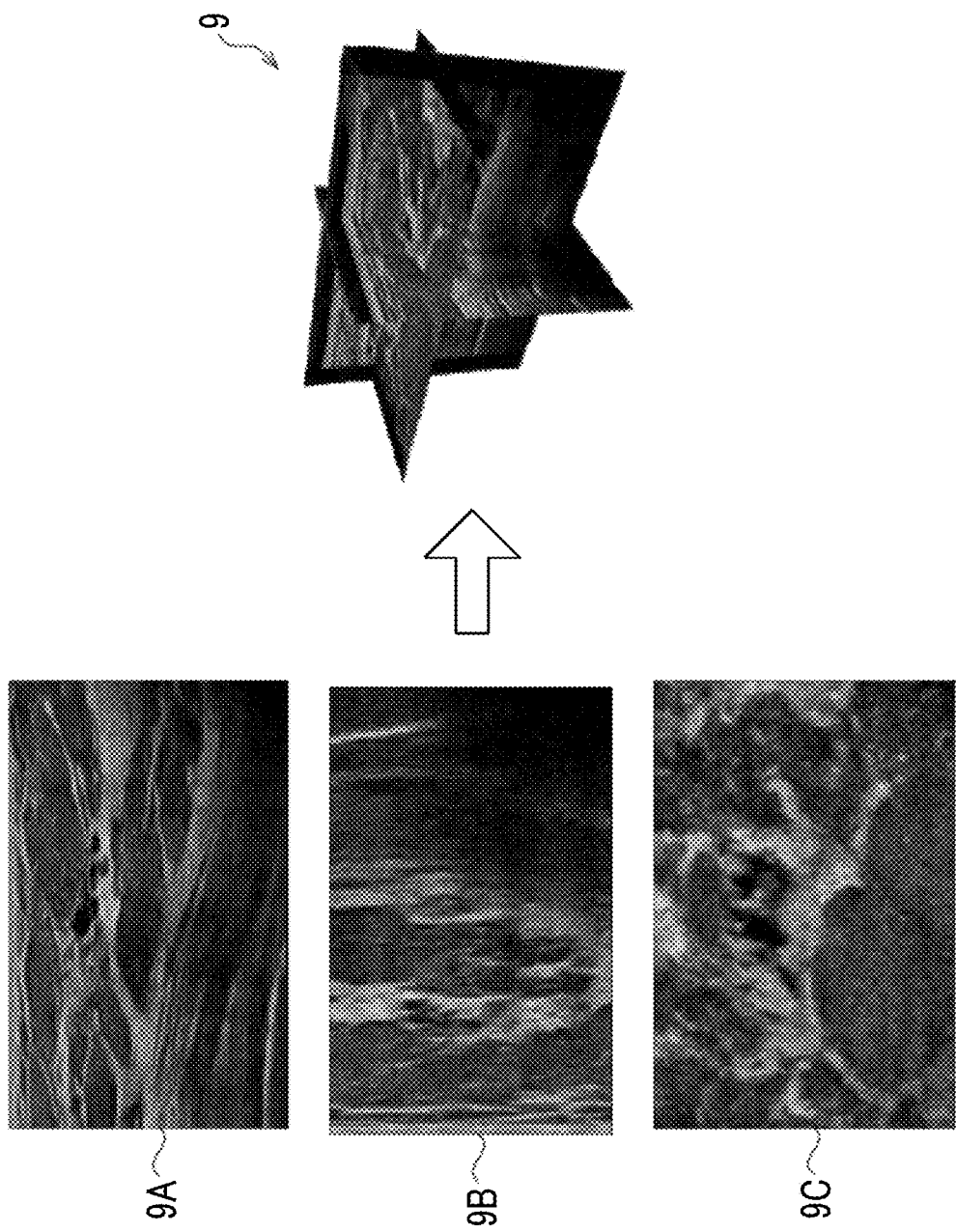
FIG. 7 is a diagram illustrating a combination example of ultrasound images.

FIG. 7 is a diagram illustrating a combination example of ultrasound images. The controller 20 generates an image 9 which is an ultrasound image three-dimensionally representing a state inside the breast, for example, by combining images 9A, 9B, and 9C which are ultrasound images individually captured. Therefore, a doctor can perform a more accurate diagnosis by using the image 9 that three-dimensionally displays the state inside the breast, as compared with a case of performing diagnosis of the state inside the breast by individually using the images 9A, 9B, and 9C.

The controller 20 stores the captured ultrasound image of the breast in the storage unit 24 or the image storage system 3, and ends the imaging processing illustrated in FIG. 6.

On the other hand, in the determination processing of step S50, in a case where it is determined that there is an application omission portion 8, the processing proceeds to step S80.

In step S80, the controller 20 controls the output unit 26 to output a warning notifying the medical worker that there is an application omission portion 8. As described above, the warning is performed in at least one form of display on a display, notification in voice, or printing on a recording medium. The controller 20 may output a warning to the medical worker by blinking or turning on a warning light provided in the output unit 26.

In a case where the breast includes the application omission portion 8 of the acoustic matching member, it is necessary to apply the acoustic matching member to the application omission portion 8. Thus, the controller 20 stops capturing of the ultrasound image and ends the imaging processing illustrated in FIG. 6.

Therefore, according to the ultrasonography apparatus 2, it is possible to confirm an application state of an acoustic impedance member on a breast before an ultrasound image is captured.

In the above description, the example of the ultrasonography apparatus 2 in which the position of the ultrasound probe 23 is controlled by the controller 20 has been described. On the other hand, a medical worker may perform scanning along the shape of the breast in a state where the medical worker can hold the ultrasound probe 23 in her/his hand. In this case, the driving unit 46 and the movement rail 49 are not necessary.

In addition, in a case where the compression plate 47 is attached to the driving unit 46, in a process between step S10 and step S20 of FIG. 6, the controller 20 may cause the compression plate 47 to move in the compression direction and cause the compression plate 47 to compress the breast by controlling the driving unit 46 via the driving section 22. In this case, in the capturing of the breast image in step S20, the breast image of the breast pressed against the loading surface 40A by the compression plate 47 is obtained.

In this case, since the breast is compressed by the compression plate 47, the ultrasound probe 23 outputs an ultrasonic wave to the breast in a state of being in contact with the upper surface 47A of the compression plate 47. As described above, the form in which the ultrasound probe 23 is brought into contact with the upper surface 47A of the compression plate 47 that compresses the breast can be regarded as a form in which the ultrasound probe 23 is in contact with the breast through the compression plate 47. Therefore, the form is included in an example of a form in which the ultrasound probe 23 is brought into contact with the breast.

Since the ultrasound probe 23 outputs an ultrasonic wave in a state of being in contact with the upper surface 47A of the compression plate 47, in order to reduce a difference in acoustic impedance between the ultrasound probe 23 and the upper surface 47A of the compression plate 47, the acoustic matching member is also applied to the upper surface 47A of the compression plate 47. In a case where the application omission portion 8 of the acoustic matching member is present on the upper surface 47A of the compression plate 47, the ultrasound image at a position corresponding to the application omission portion 8 becomes unclear. Thus, in step S40, the controller 20 detects the application omission portion 8 of the acoustic matching member from a range of the upper surface 47A of the compression plate 47 included in the breast image.

In a case where the breast is compressed by the compression plate 47 in this manner, in a case where a degree of close contact of the compression plate 47 with the breast is non-uniform, air bubbles may be generated between the breast and the acoustic matching member. In a case where air bubbles are generated between the breast and the acoustic matching member, an acoustic impedance changes in a portion of the air bubbles, and this may cause the ultrasound image to become unclear as in the application omission portion 8 of the acoustic matching member.

In addition, in a case where the degree of close contact of the compression plate 47 with the breast is non-uniform, a thickness of the acoustic matching member applied to the breast may change, and as a result, a wrinkle pattern may be generated on the acoustic matching member. In addition, for example, a wrinkle pattern may also be generated on the acoustic matching member due to a defect of the acoustic matching member, such as a breakage of a gel used as the acoustic matching member. Such a pattern is also a factor of changing the acoustic impedance, and thus this may cause the ultrasound image to become unclear as in the application omission portion 8 of the acoustic matching member.

Therefore, in step S40, the controller 20 may detect a pattern generation portion due to air bubbles and the acoustic matching member in addition to the application omission portion 8 of the acoustic matching member, from a range of the breast image included in the contour of the compressed breast. A known image processing method is used to detect a pattern due to air bubbles or the acoustic matching member.

As described above, a pattern due to air bubbles and the acoustic matching member is likely to be generated in a case where the degree of close contact of the compression plate 47 with the breast is non-uniform. Therefore, detecting a pattern generation portion due to air bubbles and the acoustic matching member is also detecting a caution portion where the degree of close contact between the acoustic matching member and at least one of the breast or the compression plate 47 is different from other portions.

The controller 20 detects the application omission portion 8 of the acoustic matching member through the compression plate 47. Thus, it is preferable that the compression plate 47 has transparency such that the acoustic matching member applied to the breast can be confirmed.

In the determination processing of step S50 of FIG. 6, in a case where it is determined that there is an application omission portion 8 in a state where the breast is compressed by the compression plate 47, after outputting a warning or before outputting a warning in step S80, the controller 20 releases the breast compression force of the compression plate 47 by moving the compression plate 47 in the compression release direction, by controlling the driving unit 46 via the driving section 22.

On the other hand, in a state where a pattern is generated due to air bubbles and the acoustic matching member, in a case where the breast is recompressed by the compression plate 47, generation of a pattern due to air bubbles or the acoustic matching member may be eliminated. Therefore, the controller 20 may release the breast compression force of the compression plate 47 and then recompress the breast by moving the compression plate 47 in the compression direction, by controlling the driving unit 46 via the driving section 22. The compression force of the compression plate 47 at a time of the initial compression of the breast may be the same as or different from the compression force of the compression plate 47 at a time of the recompression of the breast.

In a case where the breast compression force of the compression plate 47 is released, the controller 20 may move the compression plate 47 in the compression release direction to a position at which the compression plate 47 is not in contact with the breast. On the other hand, in a case where the compression plate 47 is moved to a position at which the compression force decreases to a range of 10% to 30% of the compression force before moving the compression plate 47 in the compression release direction and then the breast is recompressed, generation of a pattern due to air bubbles and the acoustic matching member may be eliminated.

Therefore, the controller 20 compresses the breast with a preparatory compression force (for example, 150 [N]) that is lowered from a defined compression force (for example, 200 [N]), which is a final breast compression force, in a range of 10% to 30%, and detects the presence or absence of a pattern due to air bubbles and the acoustic matching member. In a case where a pattern due to air bubbles and the acoustic matching member is not detected, the controller 20 may further move the compression plate 47 in the compression direction such that the breast is compressed with the specified compression force. On the other hand, in a case where a pattern due to air bubbles and the acoustic matching member is detected, the controller 20 loosens the compression force until the breast compression force becomes a compression force (for example, 105 [N]) that is lowered from the preparatory compression force in a range of 10% to 30%. In this state, the controller 20 recaptures a breast image by controlling the camera 28, and detects the presence or absence of a pattern due to air bubbles and the acoustic matching member. In a case where a pattern due to air bubbles and the acoustic matching member is not detected from the breast image, the controller 20 moves the compression plate 47 in the compression direction until the breast compression force reaches the specified compression force. On the other hand, in a case where a pattern due to air bubbles and the acoustic matching member is detected, the controller 20 moves the compression plate 47 in the compression release direction to loosen the breast compression force, and recaptures a breast image. Then, control of detecting the presence or absence of a pattern due to air bubbles and the acoustic matching member is repeated.

A breast compression range by the compression plate 47 varies depending on a type of the compression plate 47 attached to the driving unit 46. Therefore, for example, a barcode label for identifying the type of the compression plate 47 may be attached to the compression plate 47, and the barcode label may be imaged using the camera 28.

Each time the type of the compression plate 47 is changed, the controller 20 specifies the type of the compression plate 47 attached to the driving unit 46 from the content of the barcode label imaged by the camera 28. Then, the controller 20 acquires a breast compression range corresponding to the type of the compression plate 47 by referring to a correspondence table that defines a correspondence relationship between the type of the compression plate 47 and the breast compression range. The correspondence table that defines the correspondence relationship between the type of the compression plate 47 and the breast compression range may be stored in, for example, the ROM 20B in advance.

An example in which a barcode label attached to the compression plate 47 is read by the camera 28 has been described above. On the other hand, a barcode reader (not illustrated) may be provided in the ultrasonography apparatus 2, and a barcode label attached to the compression plate 47 may be read by the barcode reader. In a case where a barcode label is not attached to the compression plate 47, a medical worker may input the type of the compression plate 47 via the operation unit 27.

In this way, by specifying the type of the compression plate 47 attached to the driving unit 46, it is possible to set a detection range of the application omission portion 8 according to the type of the compression plate 47.

Modification Example of First Embodiment

In the processing of step S70 of the imaging processing illustrated in FIG. 6, the controller 20 performs control of causing the ultrasound probe 23 to scan the entire breast along the shape of the breast in a state where the ultrasound probe 23 is in contact with the breast and capturing an ultrasound image of the entire breast.

On the other hand, in some situations, it may be desired to capture an ultrasound image of only a specific portion of the breast instead of capturing an ultrasound image of the entire breast.

In order to respond to such an imaging request, the ultrasonography apparatus 2 has a partial imaging mode for capturing an ultrasound image of a portion designated in advance.

Figure 8:
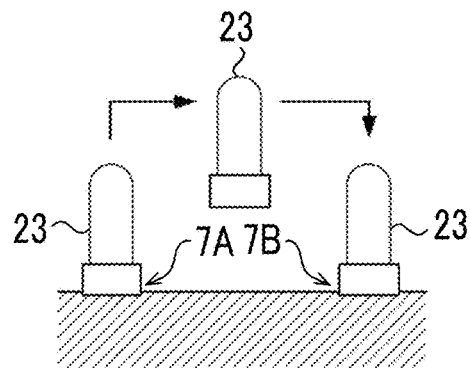
FIG. 8 is a diagram illustrating an operation example of an ultrasound probe.

FIG. 8 is a diagram illustrating an operation example of the ultrasound probe 23 in the partial imaging mode. For convenience of description, for example, it is assumed that positions 7A and 7B are designated as portions at which capturing of ultrasound images is to be performed.

In the partial imaging mode, in step S60 of the imaging processing illustrated in FIG. 6, the controller 20 moves the ultrasound probe 23 to the position 7A which is a portion designated in advance. After capturing an ultrasound image at the position 7A in step S70, the controller 20 moves the ultrasound probe 23 in the upward direction as illustrated in FIG. 8, and moves the ultrasound probe 23 to a position facing the position 7B in a state where the ultrasound probe 23 is away from the breast. From this state, the controller 20 moves the ultrasound probe 23 in the downward direction to bring the ultrasound probe 23 into contact with the breast, and captures an ultrasound image at the position 7B.

In the partial imaging mode, since the ultrasound images of the breast are captured at the positions 7A and 7B, it is not necessary to apply the acoustic matching member to the entire range within the contour of the breast. It is sufficient that the acoustic matching member is applied at least in a range of the positions 7A and 7B.

Figure 9:
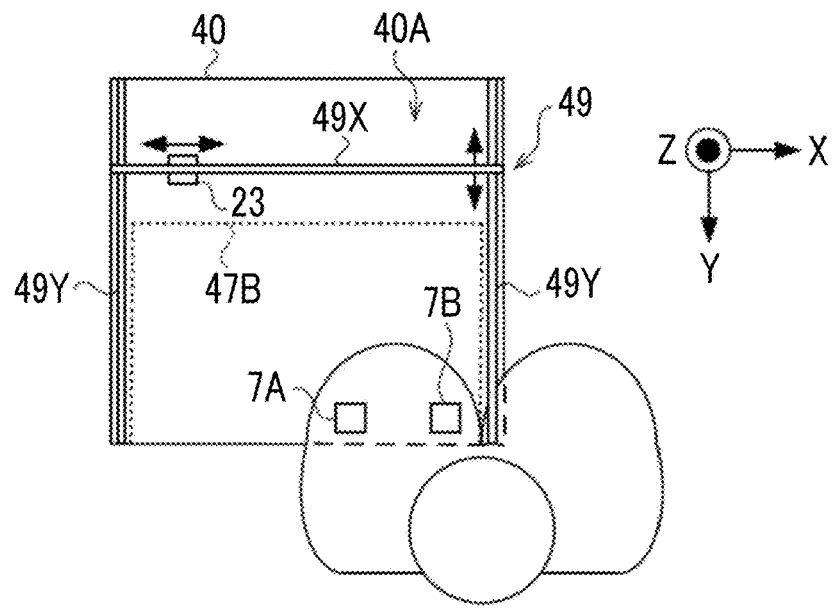
FIG. 9 is a diagram illustrating an example of a designated location at which an ultrasound image is captured.

FIG. 9 is a diagram illustrating an example in which an examinee whose a breast is placed on the loading surface 40A is viewed from a position facing the loading surface 40A of the imaging table 40 in the Z-axis direction. In a case of the example illustrated in FIG. 9, in step S40 of the imaging processing illustrated in FIG. 6, the controller 20 may detect the application omission portion 8 of the acoustic matching member from a range of the positions 7A and 7B. The designated positions indicating portions designated in advance, such as the positions 7A or the position 7B, are an example of a predetermined range set as a diagnosis location. The designated position is designated by, for example, a medical worker. That is, the medical worker can individually capture an ultrasound image of a portion of the breast that the medical worker particularly wants to confirm.

In the examples illustrated in FIG. 8 and FIG. 9, the two portions of the positions 7A and 7B are set as the designated positions. On the other hand, the number of designated positions is not limited, and the designated position may be one or three or more.

Second Embodiment

In a second embodiment, a medical imaging system 1A in which a radiography system 4 is added to the medical imaging system 1 illustrated in FIG. 1 will be described.

Figure 10:
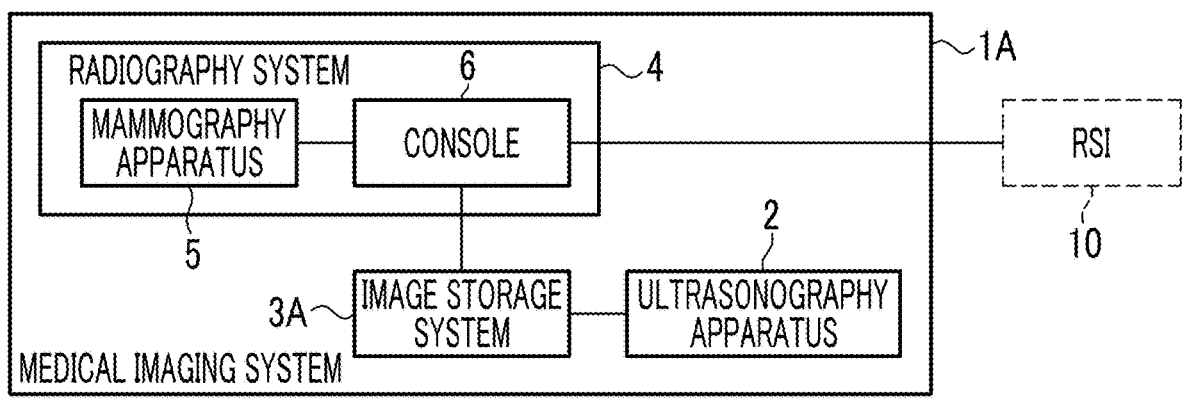
FIG. 10 is a diagram illustrating a configuration example of a medical imaging system according to a second embodiment.

FIG. 10 is a diagram illustrating a configuration example of a medical imaging system 1A according to a second embodiment. The medical imaging system 1A includes the ultrasonography apparatus 2 illustrated in FIG. 1, a radiography system 4, and an image storage system 3A obtained by expanding the image storage system 3 illustrated in FIG. 1. Further, the radiography system 4 includes a mammography apparatus 5 and a console 6.

The mammography apparatus 5 is an apparatus that irradiates a breast of an examinee compressed by the compression plate 47 with radiation R (for example, X-rays: refer to FIG. 12) and captures a radiation image of the breast. The mammography apparatus 5 is realized by a housing common to the ultrasonography apparatus 2 illustrated in FIG. 4. That is, the mammography apparatus 5 also has the functions of the ultrasonography apparatus 2 described in the first embodiment.

The console 6 is an operation console that is used to operate the mammography apparatus 5 and is connected to, for example, the mammography apparatus 5 and the image storage system 3A.

The image storage system 3A is a system that stores ultrasound images captured by the ultrasonography apparatus 2 and radiation images captured by the mammography apparatus 5. The image storage system 3A extracts an ultrasound image and a radiation image corresponding to a request from the console 6 from the stored ultrasound images and the stored radiation images, and transmits the extracted ultrasound image and the extracted radiation image to the console 6.

The console 6 has a function of controlling the mammography apparatus 5 by using a capturing order and various kinds of information acquired from a radiology information system (RIS) 10 via a communication line such as a LAN, an instruction received from the medical worker via the operation unit 27, and the like.

Figure 11:
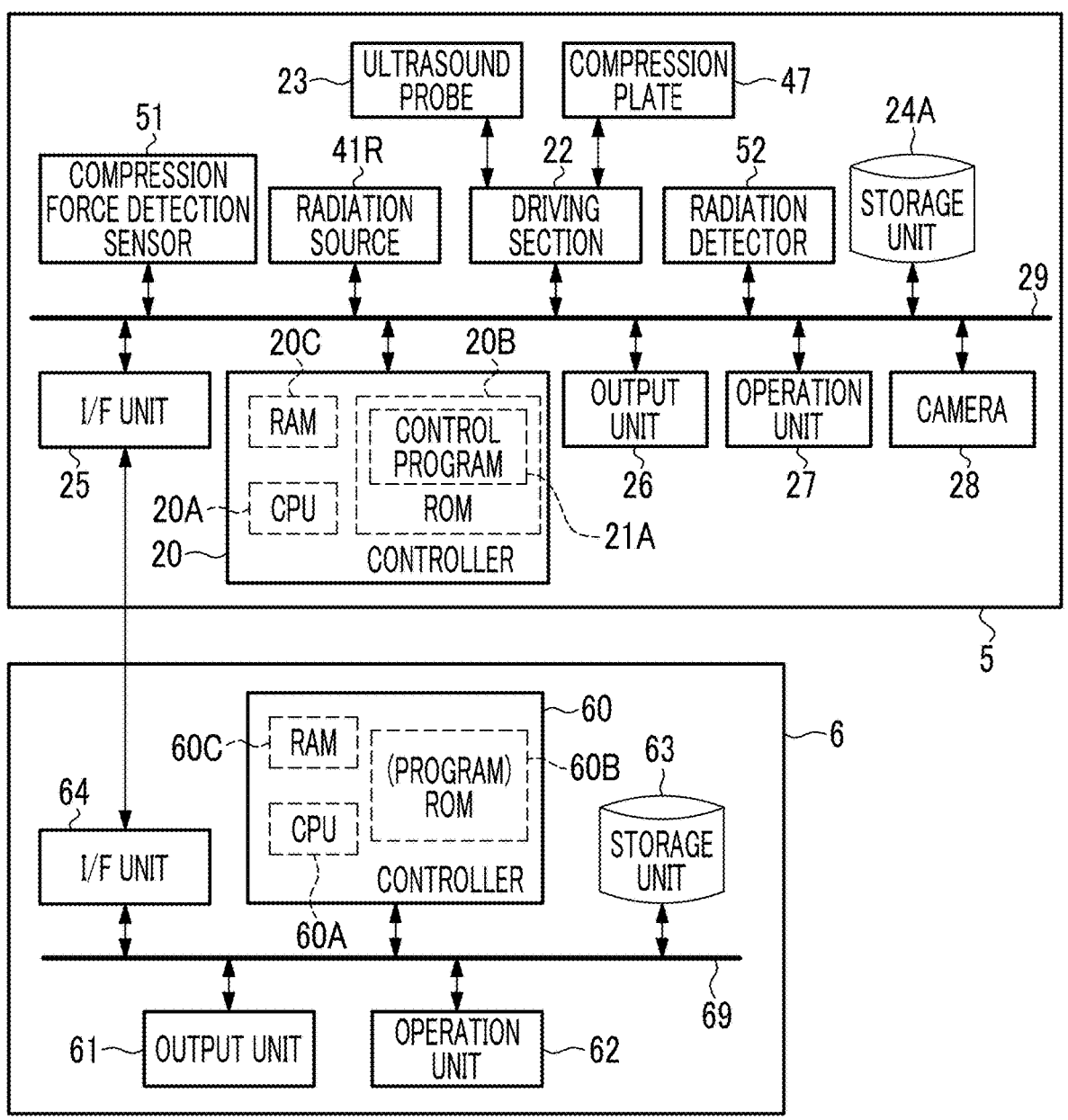
FIG. 11 is a diagram illustrating a configuration example of a mammography apparatus and a console.

FIG. 11 is a diagram illustrating a configuration example of the mammography apparatus 5 and the console 6. The mammography apparatus 5 also has the functions of the ultrasonography apparatus 2. Thus, the mammography apparatus 5 includes, in addition to the configuration of the ultrasonography apparatus 2 illustrated in FIG. 2, a compression force detection sensor 51, a radiation source 41R, a radiation detector 52, and a compression plate 47. In addition, the control program 21 and the storage unit 24 in FIG. 2 are respectively replaced with a control program 21A and a storage unit 24A.

The compression force detection sensor 51 has a function of detecting a compression force of the compression plate 47 that compresses the breast.

The radiation source 41R irradiates the breast with radiation R under a control of the controller 20 in response to the instruction from the console 6.

The radiation detector 52 detects the radiation R passing through the breast which is a subject. The radiation detector 52 is disposed in the imaging table 40. In the mammography apparatus 5 according to the present embodiment, in a case of capturing a radiation image, a breast of an examinee is positioned on the loading surface 40A of the imaging table 40 by a medical worker. The loading surface 40A with which the breast of the examinee comes into contact is made of, for example, carbon in terms of transmittance and intensity of the radiation R.

The storage unit 24A stores the captured ultrasound images, the captured radiation images, various information, and the like.

The compression plate 47 in the mammography apparatus 5 is formed of a material having excellent transmittance for the radiation R. Further, the compression plate 47 is preferably formed of a material that easily propagates the ultrasonic waves output from the ultrasound probe 23. Examples of the material forming the compression plate 47 include resins such as polymethylpentene, polycarbonate, acrylic, and polyethylene terephthalate. In particular, polymethylpentene is suitable as the material forming the compression plate 47 since polymethylpentene has low rigidity, high elasticity, and high flexibility and has suitable values for acoustic impedance that affects the reflectance of ultrasonic waves and an attenuation coefficient that affects the attenuation of ultrasonic waves. The member forming the compression plate 47 is not limited to the above-mentioned example. For example, the member forming the compression plate 47 may be a film-shaped member.

The control program 21A is a program that is read by the CPU 20A, which is an example of a processor, in order to perform control related to the capturing of an ultrasound image and the capturing of a radiation image.

The console 6 is configured by using a server computer as an example. As illustrated in FIG. 11, the console 6 includes a controller 60, an output unit 61, an operation unit 62, a storage unit 63, and an I/F unit 64. The controller 60, the output unit 61, the operation unit 62, the storage unit 63, and the I/F unit 64 are connected to each other via a bus 69 such that various kinds of information can be exchanged.

The controller 60 controls the overall operation of the console 6. The controller 60 includes a CPU 60A, a ROM 60B, and a RAM 60C. Various programs and the like executed by the CPU 60A are stored in the ROM 60B in advance. The RAM 60C is used as a temporary work area of the CPU 60A.

The output unit 61 outputs information processed by the controller 60 to the medical worker.

The operation unit 62 is used by the medical worker to input instructions, various types of information, and the like related to capturing of a radiation image, including an irradiation instruction of the radiation R. Therefore, the operation unit 62 includes at least an irradiation instruction button that is pressed by the medical worker to input an instruction to emit the radiation R. An operation form of the operation unit 62 is not limited, and, for example, an operation by a switch, a touch panel, a touch pen, a mouse, or the like can be received.

The storage unit 63 stores the radiation images captured by the mammography apparatus 5, various kinds of information, and the like. The storage unit 63 is an example of a storage device that maintains stored information even in a case where power supplied to the storage unit 63 is cut off. For example, a semiconductor memory such as an SSD is used, or a hard disk may be used.

The I/F unit 64 transmits and receives various kinds of information to and from the mammography apparatus 5 connected to, for example, a communication line such as LAN, the RIS 10, and the image storage system 3A using wireless communication or wired communication. For example, the console 6 receives a radiation image captured by the mammography apparatus 5 via the I/F unit 64, transmits the received radiation image to the image storage system 3A via the I/F unit 64, and stores the radiation image in the image storage system 3A.

Figure 12:
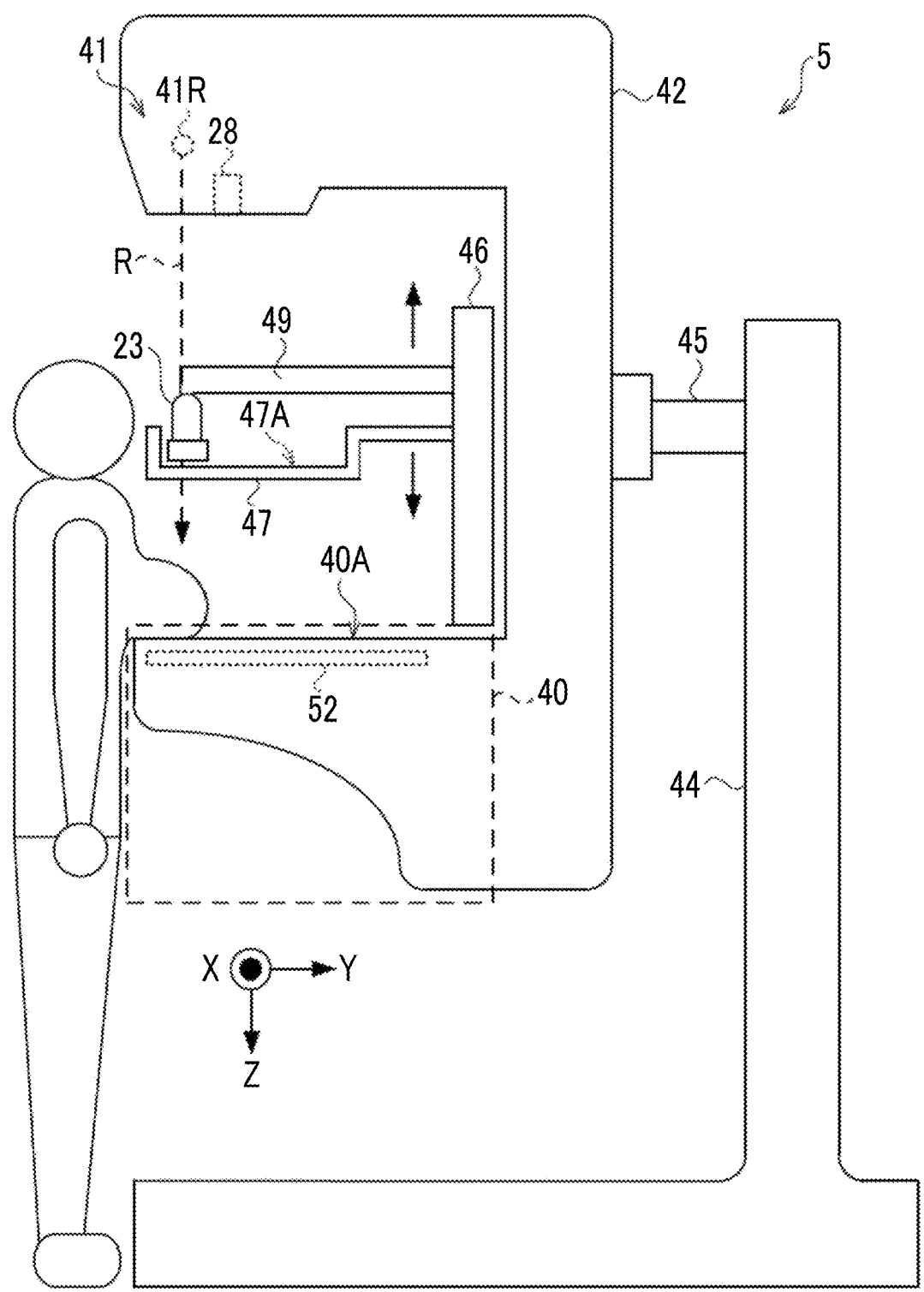
FIG. 12 is a diagram illustrating an example of an external appearance of the mammography apparatus.

FIG. 12 is a diagram illustrating an example of an external appearance of the mammography apparatus 5 in a case where the mammography apparatus is viewed from a side. The mammography apparatus 5 captures a radiation image of the compressed breast of the examinee, and the compression plate 47 is attached to the driving unit 46.

In the mammography apparatus 5 illustrated in FIG. 12, the radiation source 41R and the radiation detector 52 are added to the apparatus configuration of the ultrasonography apparatus 2 illustrated in FIG. 4.

The mammography apparatus 5 includes the radiation source 41R in the imaging unit 41, and irradiates the breast of the examinee with radiation R from the radiation source 41R. The radiation detector 52 detects the radiation R passing through the breast which is a subject. As illustrated in FIG. 12, the radiation detector 52 is disposed in the imaging table 40 below the loading surface 40A of the imaging table 40.

The mammography apparatus 5 can capture an image of the breast of the examinee in a state where the examinee is sitting on a chair (including a wheelchair) or the like (sitting state) in addition to a state where the examinee is standing (standing state).

Next, an operation of the mammography apparatus 5 that captures an ultrasound image of the breast while confirming an application state of the acoustic matching member and captures a radiation image of the breast will be described in detail.

Figure 13:
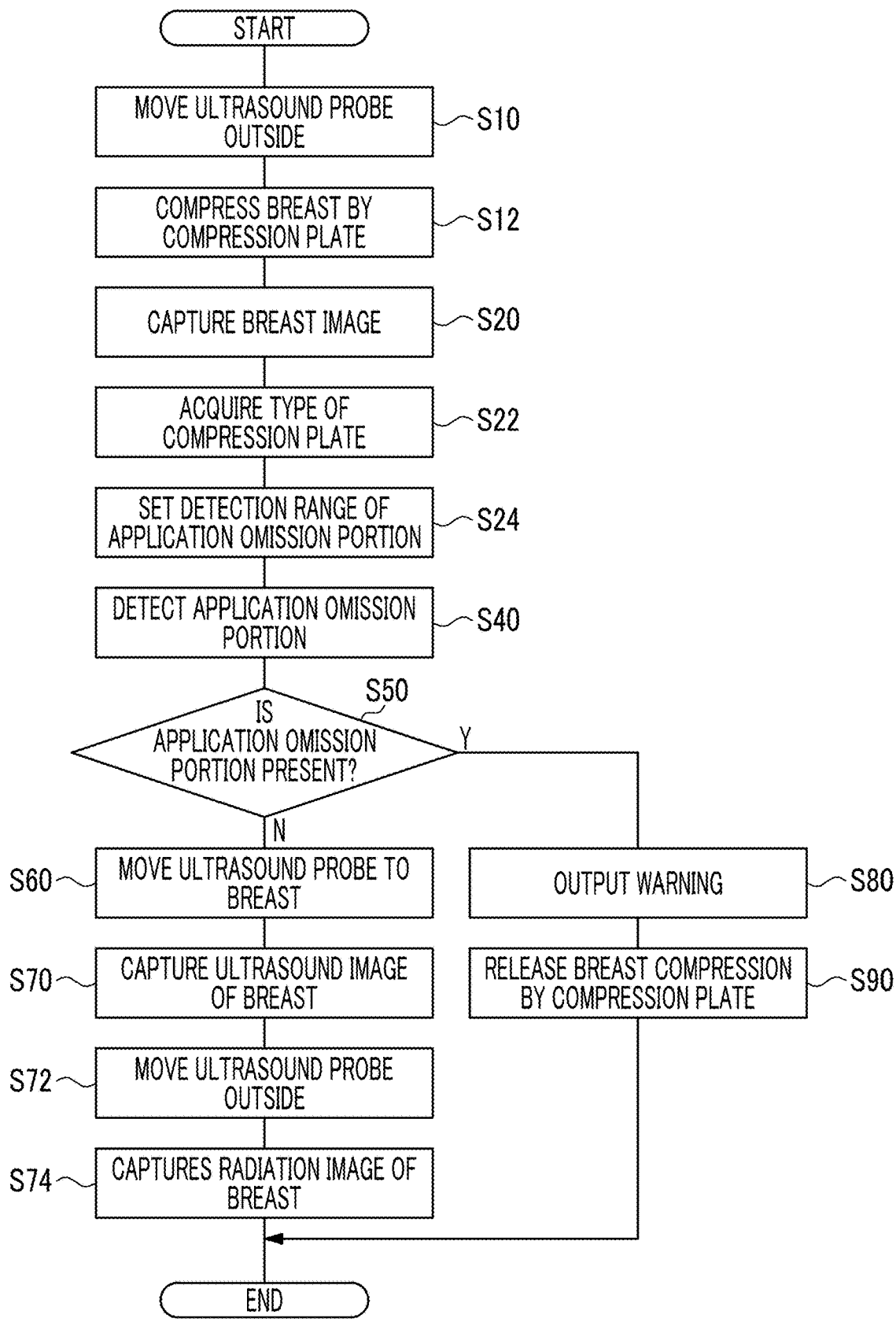
FIG. 13 is a flowchart illustrating an example of a flow of imaging processing executed by the mammography apparatus.

FIG. 13 is a flowchart illustrating an example of a flow of imaging processing executed by the mammography apparatus 5 in a case where an instruction to start capturing of an ultrasound image and a radiation image of the breast is received according to an operation of a medical worker via the console 6. The CPU 20A of the mammography apparatus 5 reads the control program 21A from the ROM 20B and executes imaging processing.

The imaging processing illustrated in FIG. 13 is different from the imaging processing illustrated in FIG. 6 in that step S12, step S22, step S24, step S72, step S74, and step S90 are added, and the other processing is the same. Therefore, in the following, the imaging processing will be described with a focus on the added processing.

After the ultrasound probe 23 is moved outside the imaging range of the camera 28 in the processing of step S10, processing of step S12 is executed.

In step S12, the controller 20 moves the compression plate 47 in the compression direction and compress the breast by the compression plate 47 by controlling the driving unit 46 via the driving section 22.

After a breast image is captured by the processing of step S20, processing of step S22 is executed.

In step S22, the controller 20 reads a barcode label attached to the compression plate 47 by a barcode reader (not illustrated) provided in the mammography apparatus 5, and acquires a type of the compression plate 47. The barcode reader is provided at a position at which the barcode label can be read, for example, in a state where the compression plate 47 is attached to the driving unit 46.

In step S24, the controller 20 acquires position information indicating a breast compression range by the compression plate 47 attached to the driving unit 46 by referring to the above-described correspondence table that defines a correspondence relationship between the type of the compression plate 47 and the breast compression range. The controller 20 sets a detection range of the application omission portion 8 by using the acquired position information. That is, the position information acquired from the correspondence table that defines the correspondence relationship between the type of the compression plate 47 and the breast compression range is an example of a predetermined range set as a diagnosis location.

In the determination processing in step S50, in a case where it is determined that there is no application omission portion 8 of the acoustic matching member within the breast compression range, in step S60 and step S70, the controller 20 captures an ultrasound image of the breast by using the ultrasound probe 23 through the compression plate 47, and the processing proceeds to step S72.

In step S72, the controller 20 moves the ultrasound probe 23 outside an imaging range of the radiation image such that the ultrasound probe 23 is not included in the imaging range of the radiation image, by controlling the driving unit 46 via the driving section 22. For example, position information indicating a position outside the imaging range of the radiation image is stored in advance in the ROM 20B.

In step S74, the controller 20 controls the radiation source 41R to start emission of radiation R, captures a radiation image of the breast compressed by the compression plate 47, and ends the imaging processing.

On the other hand, in the determination processing of step S50, in a case where it is determined that there is an application omission portion 8 of the acoustic matching member within the breast compression range, the controller 20 executes processing of step S80, and proceeds to step S90.

In this case, since the application omission portion 8 of the acoustic matching member is detected in the range set as the diagnosis location, capturing of an ultrasound image and a radiation image is stopped. Therefore, in step S90, the controller 20 moves the compression plate 47 in the compression release direction to loosen the breast compression force of the compression plate 47 by controlling the driving unit 46 via the driving section 22, and stops capturing of an ultrasound image and a radiation image.

As described in the first embodiment, after the breast compression force is loosened, in a case where a pattern due to air bubbles and the acoustic matching member is not detected in a state where the breast is recompressed, the controller 20 may continue capturing of an ultrasound image and a radiation image by executing processing after step S60.

In the imaging processing illustrated in FIG. 13, the breast compression range by the compression plate 47 is set as the detection range of the application omission portion 8. On the other hand, a maximum movement range of the ultrasound probe 23 may be set as the detection range of the application omission portion 8.

As described above, the mammography apparatus 5 confirms an application state of the acoustic impedance member on the breast before capturing an ultrasound image, and captures a radiation image and an ultrasound image in a case where there is no application omission portion 8. In the related art, after an ultrasound image and a radiation image of the breast are captured, the ultrasound image becomes unclear due to the application omission portion 8 of the acoustic matching member. On the other hand, according to the present disclosure, it is possible to suppress an occurrence of a situation where the breast of the examinee is recompressed and capturing is performed again, and thus, a burden on the examinee is reduced.

The processing of step S72 and step S74 illustrated in FIG. 13 may be moved between processing of step S50 and processing of step S60, and an ultrasound image of the breast may be captured after a radiation image of the breast is captured.

In this case, the controller 20 may specify, from the radiation image of the breast, a portion that is considered to be preferably examined in more detail by ultrasonic waves, and may set a range of the specified portion as the detection range of the application omission portion 8. The controller 20 performs diagnosis of the radiation image using, for example, a diagnosis method using a computer, such as computer-aided diagnosis (CAD).

As described above, aspects of the medical imaging systems 1 and 1A have been described using the embodiments. On the other hand, the aspects of the disclosed medical imaging systems 1 and 1A are examples, and the aspects of the medical imaging systems 1 and 1A are not limited to the range described in the embodiments. Various modifications and improvements can be added to the exemplary embodiments without departing from the scope of the present disclosure, and the exemplary embodiments to which the modifications or improvements are added are also included in the technical scope of the present disclosure.

For example, the internal processing order in the flowcharts illustrated in FIG. 6 and FIG. 13 may be changed without departing from the spirit of the present disclosure.

In the embodiments, for example, a form in which the imaging processing illustrated in FIG. 6 and FIG. 13 is implemented by software processing has been described. On the other hand, processing equivalent to the flowchart of the imaging processing may be performed by hardware. In this case, the processing speed can be increased as compared with a case where the imaging processing is implemented by software processing.

In the embodiments above, the term "processor" refers to hardware in a broad sense. Examples of the processor include general processors (e.g., CPU 20A) and dedicated processors (e.g., GPU: Graphics Processing Unit, ASIC: Application Specific Integrated Circuit, FPGA: Field Programmable Gate Array, and programmable logic device).

Further, the operation of the processor in the embodiments may be performed not only by one processor but also by cooperation of a plurality of processors provided at physically separated positions. Further, the order of the operations of the processor is not limited to only the order described in the embodiments, and may be changed as appropriate.

In the embodiments, examples in which the control programs 21 and 21A are stored in the ROM 20B have been described. On the other hand, the storage destination of the control programs 21 and 21A is not limited to the ROM 20B. The control programs 21 and 21A of the present disclosure can also be provided by being recorded in a computer-readable storage medium.

For example, the control programs 21 and 21A may be provided by being recorded on an optical disk, such as a compact disk read only memory (CD-ROM), a digital versatile disk read only memory (DVD-ROM), and a blue ray disk. In addition, the control programs 21 and 21A may be provided by being recorded in a portable semiconductor memory such as a universal serial bus (USB) memory and a memory card. The ROM 20B, the CD-ROM, the DVD-ROM, the blue ray disk, the USB, and the memory card are examples of non-transitory storage media.

Further, the controller 20 may download the control programs 21 and 21A from an external apparatus connected to the communication line via the I/F unit 25 and store the downloaded control programs 21 and 21A in the ROM 20B of the controller 20. In this case, the CPU 20A of the controller 20 reads, from the ROM 20B, the control programs 21 and 21A downloaded from the external apparatus, and executes the imaging processing.

What is claimed is:
1. An ultrasonography apparatus comprising:
a compression plate that compresses a breast on an imaging table in a case where an ultrasound image is captured using an ultrasound probe, the ultrasound probe outputting an ultrasonic wave to the breast; and
a processor that is configured to:
detect, from an image obtained by capturing the breast, a region of breast to which an acoustic matching member is not applied, the acoustic matching member being a member for reducing a difference in acoustic impedance between the ultrasound probe and the breast;
effect control of outputting a warning in a case where the region is detected; and release a compression force of the compression plate that compresses the breast in a case where the warning is output.

2. The ultrasonography apparatus according to claim 1, wherein the processor is configured to detect the region from a predetermined range in the image, which is predetermined as a breast diagnosis location by using an ultrasonic wave.

3. The ultrasonography apparatus according to claim 2, further comprising:
an imaging table on which the breast is placed for imaging,
wherein the processor is configured to set the predetermined range to be a range of the breast pressed against the imaging table by the compression plate, and to detect the region.

4. The ultrasonography apparatus according to claim 2, wherein a loading surface of the imaging table on which the breast is placed is painted in a color different from a color of the breast.

5. The ultrasonography apparatus according to claim 2, wherein the processor is configured to set, each time a type of the compression plate is changed, the predetermined range to be a breast compression range that is associated in advance with each type of the compression plate to, and to detect the region.

6. The ultrasonography apparatus according to claim 2, wherein the processor is configured to set the predetermined range to be a designated location in the image, and to detect the region.

7. The ultrasonography apparatus according to claim 2, wherein the processor is configured to set the predetermined range to be a maximum movement range of the ultrasound probe in the image, and to detect the region.

8. The ultrasonography apparatus according to claim 1, wherein the processor is configured to:
detect a caution portion at which a degree of close contact between the acoustic matching member and at least one of the breast or the compression plate in a state where the breast is compressed by the compression plate is different from other portions, and
in a case where the caution portion is detected, release a compression force of the compression plate that compresses the breast and then recompress the breast by the compression plate.

9. A mammography apparatus comprising:
a radiation source that irradiates a breast with radiation; and
the ultrasonography apparatus according to claim 1.

10. The mammography apparatus according to claim 9, wherein the processor is configured to identify a breast diagnosis location by using an ultrasonic wave from a radiation image of the breast that is captured by the radiation emitted from the radiation source, and to detect the region from a range of the identified breast diagnosis location.

11. A control method comprising:
compressing, by a compression plate, a breast on an imaging table in a case where an ultrasound image is captured using an ultrasound probe, the ultrasound probe outputting an ultrasonic wave to the breast;
detecting, from an image obtained by capturing the breast, a region of breast to which an acoustic matching member is not applied, the acoustic matching member being a member for reducing a difference in acoustic impedance between the ultrasound probe and the breast;
outputting a warning in a case where the region is detected; and
releasing a compression force of the compression plate that compresses the breast in a case where the warning is output.

12. A non-transitory storage medium storing a program that causes a computer to execute a control process, the control process comprising:
compressing, by a compression plate, a breast on an imaging table in a case where an ultrasound image is captured using an ultrasound probe, the ultrasound probe outputting an ultrasonic wave to the breast;
detecting, from an image obtained by capturing the breast, a region of breast to which an acoustic matching member is not applied, the acoustic matching member being a member for reducing a difference in acoustic impedance between the ultrasound probe and the breast;
outputting a warning in a case where the region is detected; and
releasing a compression force of the compression plate that compresses the breast in a case where the warning is output.

* * * * *